United States Patent [19]

March

[11] Patent Number: 5,552,309
[45] Date of Patent: Sep. 3, 1996

[54] USE OF POLYOLS FOR IMPROVING THE INTRODUCTION OF GENETIC MATERIAL INTO CELLS

[75] Inventor: Keith L. March, Carmel, Ind.

[73] Assignee: Indiana University Foundation, Bloomington, Ind.

[21] Appl. No.: 315,974

[22] Filed: Sep. 30, 1994

[51] Int. Cl.$^6$ .............................. A01N 63/00; C12N 5/00; C12N 15/00
[52] U.S. Cl. .................................. 435/172.3; 435/235.1; 435/240.2; 435/320.1; 514/44; 424/93.1; 424/93.2; 424/426; 935/57
[58] Field of Search ................................ 424/93.1, 93.2, 424/426; 435/172.3, 320.1, 240.2; 514/44; 935/57

[56] References Cited

U.S. PATENT DOCUMENTS

| 5,118,512 | 6/1992 | O'Leary et al. | 424/549 |
| 5,298,222 | 3/1994 | O'Leary et al. | 422/28 |

OTHER PUBLICATIONS

Technical Data on Pluronic Polyol Gels, BASF Wyandotte Corporation, Parsippany, N.J.
Material Safety Data Sheet, Pluronic F127 NF (Poloxamer NF), BASF Corporation Chemicals Division, Parsippany, N.J.
Johnston, et al., *Journal of Parenteral Science and Technology*, vol. 48, No. 6, pp. 279–286 (Nov.–Dec. 1989).
Fults, et al., *Journal of Parenteral Science and Technology*, vol. 44, No. 2, pp. 58–65 (Mar.–Apr. 1990).
Schmolka, *JAOCS*, vol. 68, No. 3, pp. 206–209 (Mar. 1991).
Langer, et al., *J. Cell. Biochem.*, vol. 45, pp. 340–345 (1991).
Johnston, et al., *Pharmaceutical Research*, vol. 9, No. 3 pp. 425–434 (1992).
March, et al., *Cardio Intervention*, pp. 11–26 (1992).
Pec, et al., *Journal of Pharmaceutical Sciences*, vol. 81, No. 7, pp. 626–630 (Jul. 1992).
Simons, et al., *Nature*, vol. 359, pp. 67–70 (Sep. 3, 1992).
Gunzman, et al., *Circulation*, vol. 88, No. 4, Part 2, pp. 1–80 (Oct. 1993).
Trapnell, *Adv. Drug Del. Rev.* vol. 12, pp. 185–199 (1993).
Smith, et al., *Nature Genetics*, vol. 5, pp. 397–401 (Dec. 1993).
Yei, et al., *Human Gene Therapy*, vol. 5, pp. 731–744 (1994).

Primary Examiner—Bruce R. Campell
Attorney, Agent, or Firm—Elliot M. Olstein; Raymond J. Lillie

[57] ABSTRACT

A process for introducing an expression vehicle (e.g., plasmids, retroviral vectors, adenoviral vectors) into cells, which comprises contacting the cells with the expression vehicle and a polyol. The polyol may be a polyoxalkylene block copolymer, such as a polyoxypropylene-polyoxyethylene block copolymer. The use of the polyol provides for greater efficiency of transduction of the expression vehicle.

15 Claims, 9 Drawing Sheets

USE OF POLYOLS FOR IMPROVING THE INTRODUCTION OF GENETIC MATERIAL INTO CELLS

This invention relates to the introduction of genetic material into cells. More particularly, this invention relates to improving the introduction of genetic material into cells by contacting the cells into which the genetic material is to be introduced with the genetic material and a slow release polymer, such as a polyol.

BACKGROUND OF THE INVENTION

The development of strategies for the transfer of genes into desired cells offers new therapeutic possibilities. For example, several methods for in vivo gene transfer to the vascular wall have been explored, including reimplantation of vascular cells which have been genetically engineered in vitro (Nabel, et al., *Science*, Vol. 244, pgs. 1342–1344 (1989); Wilson, et al., *Science*, Vol. 244, pgs. 1344–1346 (1989); Dichek, et al., *Circulation*, Vol. 80, pgs. 1347–1353 (1989)) as well as direct, in vivo gene transfer using several types of gene delivery vehicles, including plasmid DNA complexes (LeClerc, et al., *J.Clin.Invest.*, Vol. 90, pgs. 936–944 (1992) Nabel, et al., *Science*, Vol. 249, pgs. 1285–1288 (1991); retroviral vectors (Nabel, et al., 1990, Flugelman, et al.,, *Circulation*, Vol. 85, pgs. 1110–1117 (1992)); Lim, et al., *Circulation*, Vol. 83, pgs. 2007–2011 (1991)), retroviral vectors (Nabel, et al., 1990; Flugelman, et al., *Circulation*, Vol. 85, pgs. 1110–1117 (1992)) and adenoviral vectors (Guzman, et al., *Circulation*, Vol. 88, pgs. 2838–2848 (1993); Lemarchand, et al., *Proc. Nat. Acad. Sci.*, Vol. 89, pgs. 6482–6486 (1992); Lee, et al., *Circ. Res.*, Vol. 73, pgs. 797–807 (1993)). In this context, the blood flow constantly dilutes the local milieu of the vessel wall at a rapid rate as compared with the finite time required for vector binding and gene transfer into cells, and several features of gene transfer to the vascular wall have been hypothesized. First, delivery of genes to specific regions of a vessel may require physical localization of vector during uptake into the vessel wall segment. Catheter-based strategies employing a variety of catheter designs are being explored for this purpose. (March, et al., *Cardio Intervention*, Vol. 2, No. 2, pgs. 11–26 (1992)). Several studies have reported successes using a dual ligature or dual-balloon approach to isolate a section of the vascular wall during transduction. (LeClerc, et al., *J.Clin.Invest.*, Vol. 90, pgs. 936–944 (1992); Nabel, et al., 1990; Lim, et al., 1991; Flugelman, et al., 1992; Lemarchand, et al., 1992; Lee, et al., 1993; Guzman, et al., 1993). Second, to the extent that localization of gene delivery to a specific region is important, maximization of specific vascular gene delivery must be accomplished. Third, the time permitted for gene transfer will be limited by pathologic alterations imposed by gene transfer; i.e., potential ischemia in the vascular distribution distal to a segmental isolation. The rate of gene transfer into vascular wall cells must be sufficiently rapid to achieve an adequate absolute level of transduction in the available time.

Gene delivery vehicles which may be employed include retroviral vectors and adenoviral vectors. Retroviral vectors may be employed for infecting dividing cells, while adenoviral vectors may be employed for infecting dividing and non-dividing cells. Adenoviral vectors have been used successfully for in vivo gene transfer of marker genes such as β-galactosidase (Stratford-Perricaudet, et al., *Hum. Gene Ther.* Vol. 1, pgs. 240–256 (1990); Mastrangeli, et al., *J. Clin, Invest.*, Vol. 91, pgs. 225–234 (1993); Englehart, et al., *Nat. Genet.*, Vol. 4, pgs. 27–34 (1993); Yei, et al. *Hum. Gene Ther.*, Vol. 5, pgs. 733–746 (1994)), the luciferase gene (Trapnell, *Adv. Drug. Del. Rev.*, Vol. 12, pgs. 185–199 (1994)), as well as potentially therapeutic genes such as ornithine transcarbamylase (Stratford-Perricaudet, et al., 1990), α-1-antitrypsin (Rosenfeld, et al., *Science*, Vol. 252, pgs. 431–434 (1991)), cystic fibrosis transmembrane conductance regulator, (Rosenfeld, et al., *Cell*, Vol. 68, pgs. 143–155 (1992); Dabner, et al., *Nature Genet.*, Vol. 1, pgs. 75–83 (1993)); Factor IX (Smith, et al., *Nature Genet.*, Vol. 5, pgs. 397–402 (1993)), dystrophin (Vincent, et al., *Nat. Genet.*, Vol. 5, pgs. 130–134 (1993)) and chimeric inhibitors of tumor necrosis factor (Kolls, et al., *Proc. Nat. Acad. Sci.*, Vol. 91, pgs. 215–219 (1994)), to a variety of organs and tissues. Initial studies of adenoviral gene transfer into the vascular wall (Lemarchand, et al., 1992; Lee, et al., 1993; Guzman, et al., 1993) have demonstrated substantially higher transduction frequency than observed using similar protocols with plasmid/liposome complexes or retroviruses. Gene delivery in these studies was accomplished only with isolation of the vascular segment to be transduced for 20 to 45 minutes to permit sufficient vector uptake.

DETAILED DESCRIPTION OF THE INVENTION

In accordance with an aspect of the present invention, there is provided a process for introducing an expression vehicle into cells. The process comprises contacting the cells with the expression vehicle and a slow release polymer, such as a polyol.

The polyol which is employed is one which is biocompatible, and which in general is capable of maintaining high pericellular concentrations of the expression vehicle.

The polyol may be cationic, anionic, or non-ionic. In one embodiment, the polyol is a non-ionic polyol.

In one embodiment, the non-ionic polyol is a polyoxyalkylene polymer, and more preferably a polyoxyalkylene block copolymer, wherein the polyoxyalkylene groups each have from 2 to 5 carbon atoms. The polyoxyalkylene polymer may have a molecular weight of from about 300 to about 40,000, preferably from about 900 to about 20,000.

In a more preferred embodiment, the polyoxyalkylene block copolymer is a polyoxypropylene-polyoxyethylene block copolymer. In one embodiment, the polyoxypropylene component is present in an amount of from about 20 to about 90 wt. % of the copolymer, and the polyoxyethylene component is present in an amount of from about 10 wt. % to about 80 wt. % of the copolymer. In a preferred embodiment, the polyoxypropylene is present in an amount of about 30 wt. % of the copolymer, and the polyoxyethylene is present in an amount of about 70 wt. % of the copolymer. An example of such a polyoxypropylene-polyoxyethylene block copolymer which may be employed in accordance with the present invention is a polyoxypropylene-polyoxyethylene block copolymer having a molecular weight of about 12,500, and sold under the trade names Pluronic F127 or Poloxamer 407 by BASF Corporation, Chemical Division, Parsippany, N.J. It is to be understood, however, that the scope of the present invention is not to be limited to any particular polyol.

In another embodiment, the polyol is an alkylene diamine/polyoxyalkylene block copolymer polyol having the following structural formula:

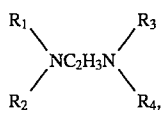

wherein each of $R_1$, $R_2$, $R_3$ and $R_4$ is a polyoxyalkylene block copolymer. The polyoxyalkylene block copolymer may be as hereinabove described, and more preferably is a polyoxypropylene-polyoxyethylene block copolymer as hereinabove described.

The alkylene diamine, in one embodiment, has from 2 to 5 carbon atoms, and preferably is ethylene diamine. In another embodiment, the alkylene diamine/polyoxyalkylene block copolymer polyol has a molecular weight of from about 300 to about 40,000, preferably from about 900 to about 20,000.

Although the scope of the present invention is not to be limited to any theoretical reasoning, it is believed that the viscosity of the polyol may provide for entrapment of the expression vehicle on or in the fluid boundary layer surrounding the target cells, so that the pericellular concentration of the expression vehicle remains elevated for an increased period of time, thereby enhancing the rate of transformation of cells. In addition, the polyol may influence directly the cell membrane in order to render it more permeable to or retentive of the expression vehicle following initial collision of the genetic material with the cells.

Genetic material which may be contained in the expression vehicle which is introduced into the cells includes, but is not limited to, nucleic acid sequences of DNA or RNA (including antisense oligonucleotides). Such nucleic acid sequences may encode a therapeutic agent. The term "therapeutic" is used in a generic sense and includes treating agents, prophylactic agents, and replacement agents.

The term "nucleic acid sequence" as used herein, means a DNA or RNA molecule, and more particularly a linear series of deoxyribonucleotides or ribonucleotides connected one to the other by phosphodiester bonds between the 3' and 5' carbons of the adjacent pentoses. Depending upon the use herein, such term includes complete and partial gene sequences, and includes polynucleotides as well.

Expression vehicles which may be introduced into the cells include, but are not limited to plasmid vectors, such as, for example, prokaryotic plasmid vectors (e.g., bacterial expression vectors), eukaryotic plasmid vectors (e.g., yeast vectors and fungal vectors), and viral plasmid vectors, including retroviral plasmid vectors, adenoviral plasmid vectors, and adeno-associated virus plasmid vectors. When the expression vehicle is a viral plasmid vector, such plasmid vector may be contained within an infectious viral vector particle, such as a retroviral vector particle, an adenoviral vector particle, or an adeno-associated virus vector particle.

In one embodiment, the expression vehicle is a viral vector particle, sometimes hereinafter referred to as a "viral vector." The viral vector may be a retroviral vector, an adenoviral vector, an adeno-associated virus vector, or a Herpes Virus vector.

In one embodiment, the viral vector is an adenoviral vector.

The adenoviral vector which is employed may, in one embodiment, be an adenoviral vector which includes essentially the complete adenoviral genome (Shenk, et al., *Curr. Top. Microbiol. Immunol.*, 111(3): 1–39 (1984)). Alternatively, the adenoviral vector may be a modified adenoviral vector in which at least a portion of the adenoviral genome has been deleted.

In one embodiment, the adenoviral vector comprises an adenoviral 5' ITR; an adenoviral 3' ITR; an adenoviral encapsidation signal; and at least one DNA sequence encoding a therapeutic agent. The vector is free of at least the majority of adenoviral E1 and E3 DNA sequences, but is not free of all of the E2 and E4 DNA sequences, and DNA sequences encoding adenoviral proteins promoted by the adenoviral major late promoter. In one embodiment, the vector is also free of at least a portion of at least one DNA sequence selected from the group consisting of the E2 and E4 DNA sequences.

In another embodiment, the vector is free of at least the majority of the adenoviral E1 and E3 DNA sequences, and is free of one of the E2 and E4 DNA sequences, and is free of a portion of the other of the E2 and E4 DNA sequences.

In still another embodiment, the gene in the E2a region that encodes the 72 kilodalton binding protein is mutated to produce a temperature sensitive protein that is active at 32° C., the temperature at which the viral particles are produced, but is inactive at 37° C., the temperature of the animal or human host. This temperature sensitive mutant is described in Ensinger, et al., *J. Virology*, 10: 328–339 (1972), Van der Vliet, et al., *J. Virology*, 15: 348–354 (1975), and Friefeld, et al., *Virology*, 124: 380–389 (1983).

In yet another embodiment, the vector is free of at least the majority of the E1 and E3 DNA sequences, is free of at least a portion of at least one DNA sequence selected from the group consisting of the E2 and E4 DNA sequences, and is free of DNA sequences encoding adenoviral proteins promoted by the adenoviral major late promoter.

Such a vector, in a preferred embodiment, is constructed first by constructing, according to standard techniques, a shuttle plasmid which contains, beginning at the 5' end, the "critical left end elements," which include an adenoviral 5' ITR, an adenoviral encapsidation signal, and an E1a enhancer sequence; a promoter (which may be an adenoviral promoter or a foreign promoter); a multiple cloning site; a poly A signal; and a DNA segment which corresponds to a segment of the adenoviral genome. The vector also may contain a tripartite leader sequence. The DNA segment corresponding to the adenoviral genome serves as a substrate for homologous recombination with a modified or mutated adenovirus, and such sequence may encompass, for example, a segment of the adenovirus 5 genome no longer than from base 3329 to base 6246 of the genome. The plasmid may also include a selectable marker and an origin of replication. The origin of replication may be a bacterial origin of replication. Representative examples of such shuttle plasmids include pAVS6, shown in FIG. 4. The DNA encoding the therapeutic agent then may be inserted into the multiple cloning site. One may amplify the expression of the DNA encoding the therapeutic agent by adding to the plasmid increased copies of the DNA encoding the therapeutic agent.

This construct is then used to produce an adenoviral vector. Homologous recombination is effected with a modified or mutated adenovirus in which at least the majority of the E1 and E3 adenoviral DNA sequences have been deleted. Such homologous recombination may be effected through co-transfection of the plasmid vector and the modified adenovirus into a helper cell line, such as 293 cells, by CaPO$_4$ precipitation. The helper cells may be contacted with the plasmid vector, the modified adenovirus, and the polyol, which aids in enabling the plasmid vector and modified adenovirus to transfect the helper cells. Upon such homologous recombination, a recombinant adenoviral vector is formed that includes DNA sequences derived from the shuttle plasmid between the NotI site and the homologous recombination fragment, and DNA derived from the E1 and E3 deleted adenovirus between the homologous recombination fragment and the 3' ITR.

In one embodiment, the homologous recombination fragment overlaps with nucleotides 3329 to 6246 of the adenovirus 5 (ATCC VR-5) genome.

Through such homologous recombination, a vector is formed which includes an adenoviral 5' ITR, an adenoviral encapsidation signal; an E1a enhancer sequence; a promoter; at least the DNA sequence which encodes a therapeutic agent; a poly A signal; adenoviral DNA free of at least the majority of the E1 and E3 adenoviral DNA sequences; and an adenoviral 3' ITR. The vector also may include a tripartite leader sequence. This vector may then be transfected into a helper cell line, such as the 293 helper cell line, which will include the E1a and E1b DNA sequences, which are necessary for viral replication, and to generate infectious adenoviral particles. The polyol, which may be as hereinabove described, may be used to aid in enabling the vector to be transfected into the helper cell line.

In one embodiment, the adenoviral vector comprises an adenoviral 5' ITR; an adenoviral 3' ITR; an adenoviral encapsidation signal; and at least one DNA sequence encoding a therapeutic agent. The vector is free of the adenoviral E1, E2, E3, and E4 DNA sequences, and the vector is free of DNA sequences encoding adenoviral proteins promoted by the adenoviral major late promoter; i.e., the vector is free of DNA encoding adenoviral structural proteins.

Such vectors may be constructed by removing the adenoviral 5' ITR, the adenoviral 3' ITR, and the adenoviral encapsidation signal, from an adenoviral genome by standard techniques. Such components, as well as a promoter (which may be an adenoviral promoter or a non-adenoviral promoter), tripartite leader sequence, poly A signal, and selectable marker, may, by standard techniques, be ligated into a base plasmid or "starter" plasmid such as, for example, pBluescript II KS-(Stratagene), to form an appropriate cloning vector. The cloning vector may include a multiple cloning site to facilitate the insertion of the DNA sequence(s) encoding the therapeutic agent(s). In general, the multiple cloning site includes "rare" restriction enzyme sites; i.e., sites which are found in eukaryotic genes at a frequency of from about one in every 10,000 to about one in every 100,000 base pairs. An appropriate vector in accordance with the present invention is thus formed by cutting the cloning vector by standard techniques at appropriate restriction sites in the multiple cloning site, and then ligating the DNA sequence encoding a therapeutic agent into the cloning vector.

The vector is then packaged into infectious, nonreplicating, recombinant adenoviral particles, using a helper adenovirus which provides the necessary encapsidation materials. Preferably the helper virus has a defective encapsidation signal in order that the helper virus will not encapsidate itself. An example of an encapsidation defective helper virus which may be employed is described in Grable, et al., *J. Virol.*, Vol. 66, pgs. 723–731 (1992).

The vector and the encapsidation defective helper virus are transfected into an appropriate cell line for the generation of infectious viral particles. The vector and helper virus are contained in the polyol, which aids in the transfection of the vector and the helper virus into the cell line. Transfection may take place by electroporation, calcium phosphate precipitation, microinjection, or through proteoliposomes. Examples of appropriate cell lines include, but are not limited to, HeLa cells or 293 (embryonic kidney epithelial) cells (ATCC No. CRL 1573).

The infectious viral particles then may be administered, in combination with the polyol, in vitro to eukaryotic cells, whereby the viral particles transfect the eukaryotic cells. The polyol may be present at a concentration from about 0.05 wt. % to about 30 wt. %, preferably from about 1 wt. % to about 20 wt. %, more preferably from about 5 wt. % to about 20 wt. %, and most preferably at about 15 wt. %. The viral particles are administered to the eukaryotic cells in an amount effective to infect the eukaryotic cells. In general, the infectious viral particles are administered in an amount of from 1 to about $10^{14}$ plaque forming units (pfu), preferably from about $10^6$ to about $10^{13}$ pfu, more preferably from about $10^6$ to about $10^{12}$ pfu. The exact dosage of administration of viral particles is dependent upon the type of eukaryotic cells to be transduced, and the therapeutic agent which is to be expressed by the eukaryotic cells upon transduction of such cells with the infectious viral particles.

Eukaryotic cells which may be transduced include, but are not limited to, aortic smooth muscle cells, vascular endothelial cells, fibroblasts, and epithelial cells of the lung, gut or vagina. Such transduced eukaryotic cells then may be administered in vivo to a host as part of a gene therapy procedure, whereby the transduced eukaryotic cells express the therapeutic agent in the host.

The present invention is particularly applicable to the treatment of diseases of the blood vessel wall. For example, infectious adenoviral vector particles which include at least one nucleic acid sequence encoding therapeutic agent for treating a disease of the blood vessel wall may be administered, in combination with a polyol, to vascular cells in vitro. The transduced vascular cells, which express the therapeutic agent, then may be re-implanted into the vascular wall, whereby such re-implanted cells express the agent for treating a disease of the blood vessel wall in vivo. For example, the adenoviral vector particle may include an antisense c-myb oligonucleotide, which is employed for inhibiting intimal arterial smooth muscle cell accumulation. Other diseases which may be treated include, but are not limited to, thrombotic/clotting tendencies, ischemia, arterial hyperproliferation/atherosclerosis/restenosis, and hypertension.

Alternatively, the infectious adenoviral particles may be administered in vivo in combination with the polyol, to a host, whereby the infectious adenoviral vector particles will infect cells in vivo in a host, thereby providing for in vivo expression of the therapeutic agent in the host. The polyol may be present in a concentration from about 0.05 wt. % to about 30 wt. %, preferably from about 1 wt. % to about 20 wt. %, more preferably from about 5 wt. % to about 20 wt. %, and most preferably at about 15 wt. %. The viral particles are administered in an amount effective to produce a therapeutic effect in a host. In one embodiment, the adenoviral vector particles may be administered in an amount of from about 1 to about $10^{14}$ plaque forming units (pfu), preferably from about $10^5$ to about $10^{13}$ pfu, and more preferably from about $10^5$ to about $10^{11}$ pfu, and most preferably from about $10^6$ to about $10^{10}$ pfu. The host may be a human or non-human host. The exact dosage of adenoviral vector particles which may be administered is dependent upon the age, sex, and weight of the patient, the therapeutic agent which is to be administered, and the severity of the disorder to be treated.

The infectious adenoviral vector particles and the polyol may be administered systemically, such as, for example, by intravenous or intraperitoneal administration, as well as by intranasal, intratracheal, or endotracheal administration.

The adenoviral vector particles and the polyol may be administered in combination with a physiologically acceptable pharmaceutical carrier. Such pharmaceutical carriers include, but are not limited to, saline solution, water, and aqueous buffers such as phosphate buffers and Tris buffers. The selection of a suitable pharmaceutical carrier is deemed to be apparent to those skilled in the art from the teachings contained herein.

DNA sequences encoding therapeutic agents may be placed into the adenoviral vector include, but are not limited to, DNA sequences encoding tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 14; genes encoding GM-CSF; genes encoding adenosine deaminase, or ADA; genes which encode cellular growth factors, such as lymphokines, which are growth factors for lymphocytes; genes encoding epidermal growth factor (EGF), and keratinocyte growth factor (KGF); genes encoding soluble CD4; Factor VIII; Factor IX; T-cell receptors; the LDL receptor, ApoE, ApoC, ApoAI and other genes involved in cholesterol transport and metabolism; the alpha-1 antitrypsin (α1AT) gene, the ornithine transcarbamylase (OTC) gene, the CFTR gene, the insulin gene, viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; tissue plasminogen activator (tPA); urinary plasminogen activator (urokinase); hirudin; nitric oxide snythesase; vasoactive peptides; and angiogenic peptides.

The DNA sequence encoding at least one therapeutic agent is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the β-actin promoter; and human growth hormone promoters. The promoter also may be the native promoter which controls the gene encoding the therapeutic agent. It is to be understood, however, that the scope of the present invention is not to be limited to specific foreign genes or promoters.

In another embodiment, the viral vector is a retroviral vector.

Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, gibbon ape leukemia virus, human immunodeficiency virus, myeloproliferative sarcoma virus, and mammary tumor virus. Preferably, the retroviral vector is an infectious but non-replication competent retrovirus; however, replication competent retroviruses may also be used.

In one embodiment, the retroviral vector may be a Moloney Murine Leukemia Virus of the LN series of vectors, such as those hereinabove mentioned, and described further in Bender, et al., *J. Virol.*, Vol. 61, pgs. 1639–1649 (1987) and Miller, et al., *Biotechniques*, Vol. 7, pgs. 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral vector includes each of these cloning sites. Such vectors are further described in U.S. patent application Ser. No. 919,062, filed Jul. 23, 1992, and incorporated herein by reference in its entirety.

When a retroviral vector including such cloning sites is employed, there may also be provided a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from the shuttle cloning vector to the retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The vector then is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, such as hereinabove described, and CaPO₄ precipitation. In one alternative, the retroviral plasmid vector may be encapsulated into a liposome, or coupled to a lipid, as hereinabove described, and then administered to a host, also as hereinabove described.

The retroviral plasmid vector then is transduced into a packaging cell line, whereby the packaging cell line becomes a producer cell line. In such transduction, the packaging cell line is contacted with the retroviral plasmid vector and the polyol which, in general, is present at a concentration from about 0.05 wt. % to about 30 wt. % preferably from about 1 wt. % to about 20 wt. %, more preferably from about 5 wt. % to about 20 wt. %, and most preferably at about 15 wt. %.

The producer cell line generates infectious retroviral vector particles which include the nucleic acid sequence(s) encoding the therapeutic agent(s). Such retroviral vector particles then may be employed, in the presence of the polyol, to transduce eukaryotic cells, either in vitro or in vivo. The transduced eukaryotic cells will express the nucleic acid sequence(s) encoding the therapeutic agent(s). The polyol may be present at concentrations such as those hereinabove described.

The retroviral vector particles may transduce the eukaryotic cells in vitro or in vivo at a multiplicity of infection of from 1 to 1,000 vectors per cell, preferably from 1 to 10 vectors per cell.

Therapeutic agents which may be encoded by at least one nucleic acid sequence contained in the viral vector particles may be those as hereinabove described. The vector also may include an antisense DNA or RNA sequence. Promoters controlling such nucleic acid sequences also may be those hereinabove described.

In another alternative, the expression vehicle and the polyol may be included as part of a sustained release matrix which provides for sustained release or delivery of the expression vehicle into a host, and provides for sustained localization and delivery of the expression vehicle proximate to the desired target cells. In general, such a matrix is in the form of a gel, and the polyol may be present in an amount of from about 30 wt. % to about 40 wt. %. The polyol may be selected from those hereinabove described.

The matrix may be administered to a host in order to produce a therapeutic effect in the host. The matrix may be administered by injection, or the matrix may be implanted surgically into the host at the site of the target cells which one desires to infect with the expression vehicle. The matrix provides for a sustained release of the expression vehicle to the target cells, and enables the expression vehicle to remain localized near the target cells for an extended period of time, thereby providing for sustained and direct delivery of the expression vehicle to the target cells.

BRIEF DESCRIPTION OF THE DRAWINGS

The invention will now be described with respect to the drawings, wherein.

EXAMPLES

The invention now will be described with respect to the following examples; however, the scope of the present invention is not intended to be limited thereby.

Example 1

A. Adenoviral Gene Transfer Vector

The adenoviral vector used in this example was a replication deficient E1a/E1b⁻, E3⁻ deletion mutant expressing a nuclear-targeted β-galactosidase gene under the control of the RSV-LTR promoter. Such vector hereinafter is referred to as Av1LacZ4. The vector was produced by recombination of the expression cassette with a cotransfected adenoviral genome in 293 cells for complementation of the E1 defect, thereby allowing virion production. Viral supernatants were harvested by 3 freeze-thaw cycles, followed by purification by ultracentrifugation through two cesium chloride gradients.

Av1LacZ4 is constructed from the adenoviral shuttle vector pAyS6. The construction of Av1LacZ4 is described in detail as follows:

(i) Construction of pAvS6

Figure 1:
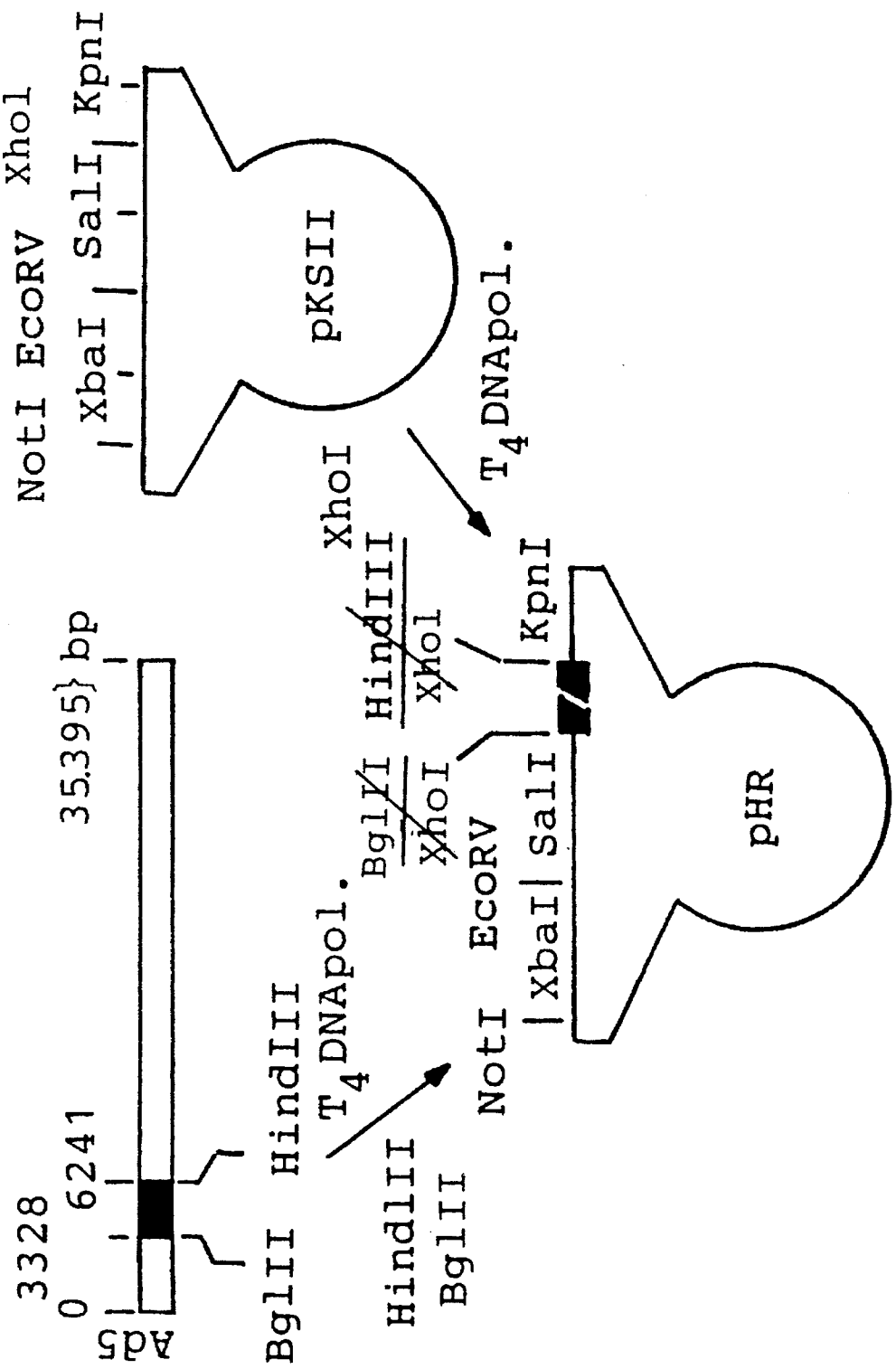
FIG. 1 is a schematic of the construction of plasmid pHR.

The adenoviral construction shuttle plasmid pAvS6 was constructed in several steps using standard cloning techniques including polymerase chain reaction based cloning techniques. First, the 2913 bp BglII, HindIII fragment was removed from Ad-dl327 and inserted as a blunt fragment into the XhoI site of pBluescript II KS-(Stratagene, La Jolla, Calif.) (FIG. 1). Ad-dl327 (Thimmappaya, et al., *Cell*, Vol. 31, pg. 543 (1983)) is identical to adenovirus 5 except that an XbaI fragment including bases 28591 to 30474 (or map units 78.5 to 84.7) of the adenovirus 5 genome, and which is located in the E3 region, has been deleted. The orientation of this fragment was such that the BglII site was nearest the T7 RNA polymerase site of pBluescript II KS⁻ and the HindIII site was nearest the T3 RNA polymerase site of Pbluescript II KS⁻. This plasmid was designated pHR. (FIG. 1).

Figure 2:
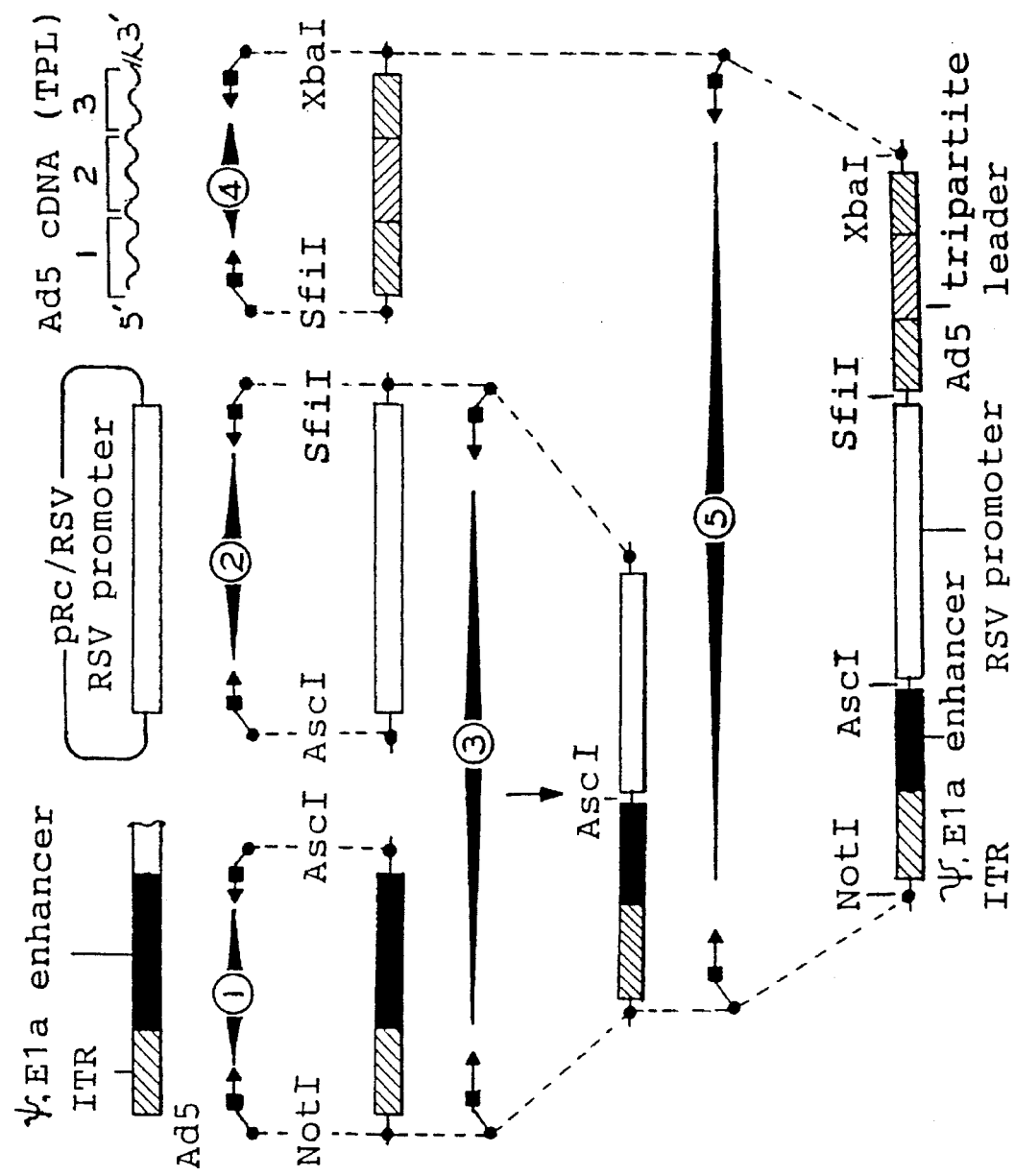
FIG. 2 is a schematic of the construction of an adenoviral vector including an ITR, an encapsidation signal, a Rous Sarcoma Virus promoter, and an adenoviral tripartite leader (TPL) sequence.

Second, the ITR, encapsidation signal, Rous Sarcoma Virus promoter, the adenoviral tripartite leader (TPL) sequence and linking sequences were assembled as a block using PCR amplification (FIG. 2). The ITR and encapsidation signal (sequences 1–392 of Ad-dl327 [identical to sequences from Ad5, Genbank accession #M73260]) were amplified (amplication 1) together from Ad-dl327 using primers containing NotI or AscI restriction sites. The Rous Sarcoma Virus LTR promoter was amplified (amplification 2) from the plasmid pRC/RSV (sequences 209 to 605; Invitrogen, San Diego, Calif.) using primers containing an AscI site and an SfiI site. DNA products from amplifications 1 and 2 were joined using the "overlap" PCR method (amplification 3) with only the NotI primer and the SfiI primer. Complementarity between the AscI containing end of each initial DNA amplification product from reactions 1 and 2 allowed joining of these two pieces during amplification. Next the TPL was amplified (amplification 4) (sequences 6049 to 9730 of Ad-dl327 [identical to similar sequences from Ad5, Genbank accession #M73260]) from cDNA made from mRNA isolated from 293 cells infected for 16 hrs. with Ad-dl327 using primers containing SfiI and XbaI sites respectively. DNA fragments from amplification reactions 3 and 4 were then joined using PCR (amplification 5) with the NotI and XbaI primers, thus creating the complete gene block.

Third, the ITR-encapsidation signal-TPL fragment was then purified, cleaved with NotI and XbaI and inserted into the NotI, XbaI cleaved pHR plasmid. This plasmid was designated pAvS6A and the orientation was such that the NotI site of the fragment was next to the T7 RNA polymerase site (FIG. 3).

Figure 3:
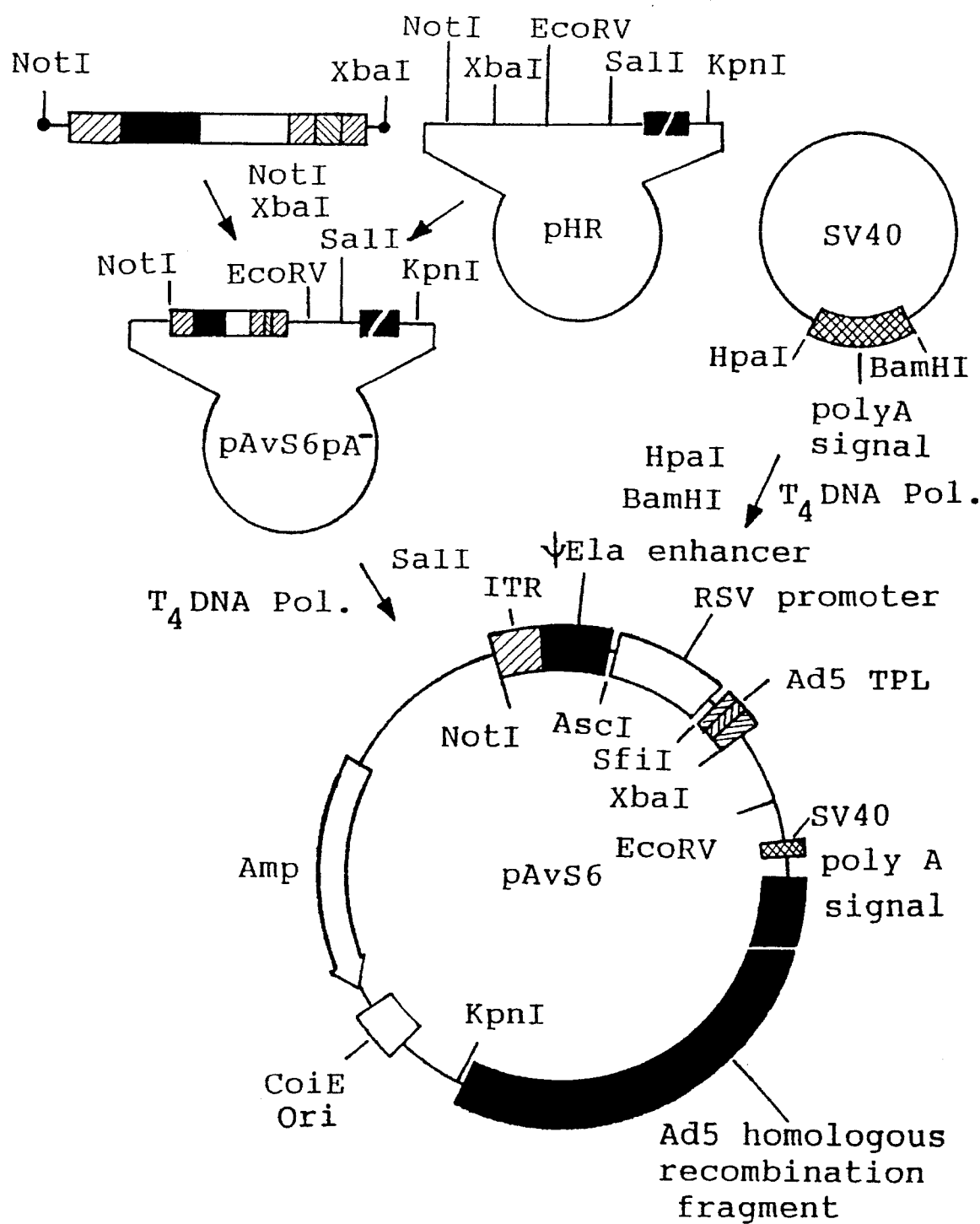
FIG. 3 is a schematic of the construction of pAvS6.
Figure 4:
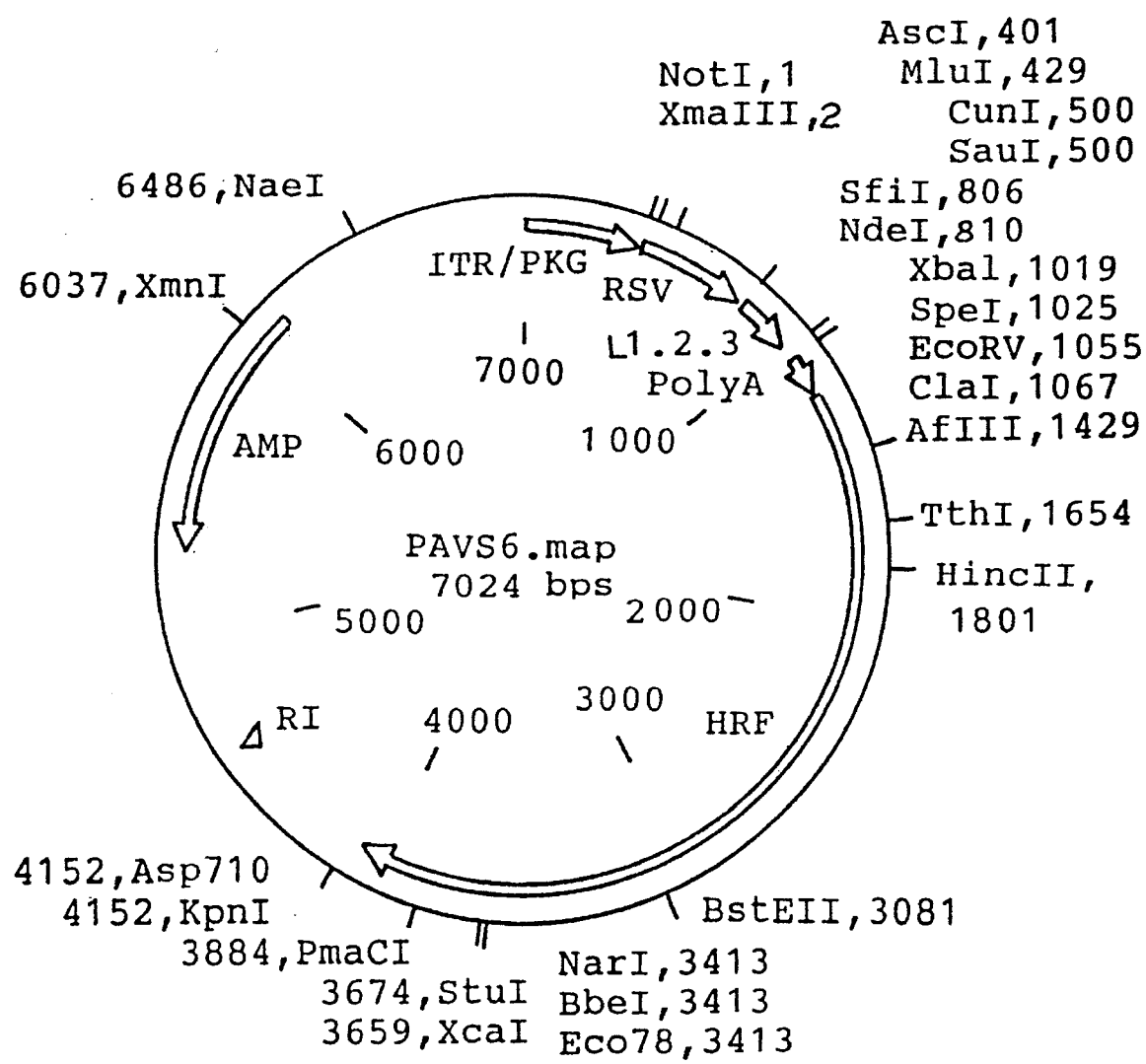
FIG. 4 is a map of plasmid pAvS6.

Fourth, the SV40 early polyA signal was removed from SV40 DNA as an HpaI-BamHI fragment, treated with T4 DNA polymerase and inserted into the SalI site of the plasmid pAvS6A-(FIG. 3) to create pAvS6 (FIGS. 3 and 4.)

(ii) Construction of Av1LacZ4.

Figure 5:
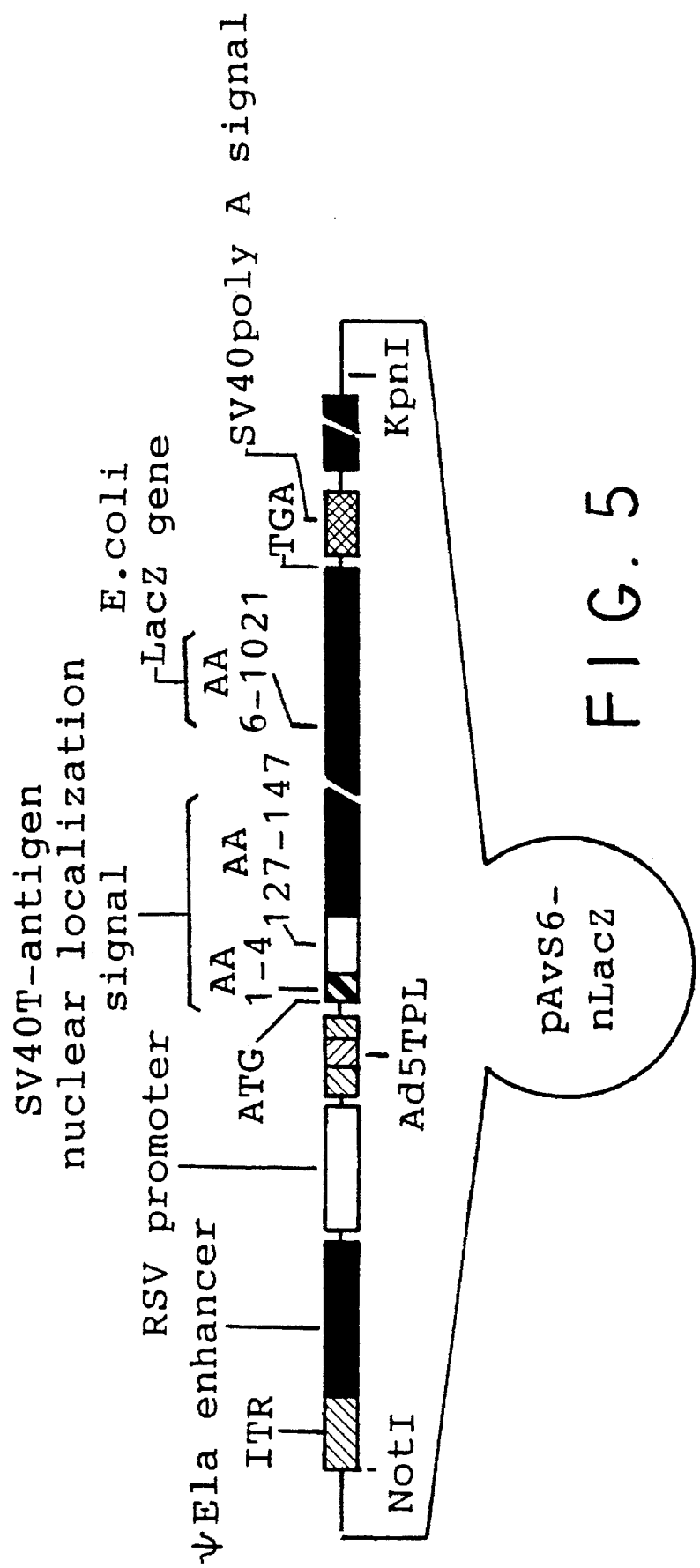
FIG. 5 is a map of plasmid pAvS6-nLacZ.

The recombinant, replication-deficient adenoviral vector Av1Lac Z4, which expresses a nuclear-targetable B-galactosidase enzyme, was constructed in two steps. First, a transcriptional unit consisting of DNA encoding amino acids 1 through 4 of the SV40 T-antigen followed by DNA encoding amino acids 127 through 147 of the SV40 T-antigen (containing the nuclear targeting peptide Pro-Lys-Lys-Lys-Arg-Lys-Val), followed by DNA encoding amino acids 6 through 1021 of E. coli B-galactosidase, was constructed using routine cloning and PCR techniques and placed into the EcoRV site of pAvS6 to yield pAvS6-nlacZ (FIG. 5).

The infectious, replication-deficient, Av1LacZ4 was assembled in 293 cells by homologous recombination. To accomplish this, plasmid pAvS6-nLacZ was linearized by cleavage with KpnI. Genomic adenoviral DNA was isolated from purified Ad-dl327 viruses by Hirt extraction, cleaved with ClaI, and the large (approximately 35 kb) fragment was isolated by agarose gel electrophoresis and purified. The ClaI fragment was used as the backbone for all first generation adenoviral vectors, and the vectors derived from it are known as Av1.

Figure 6:
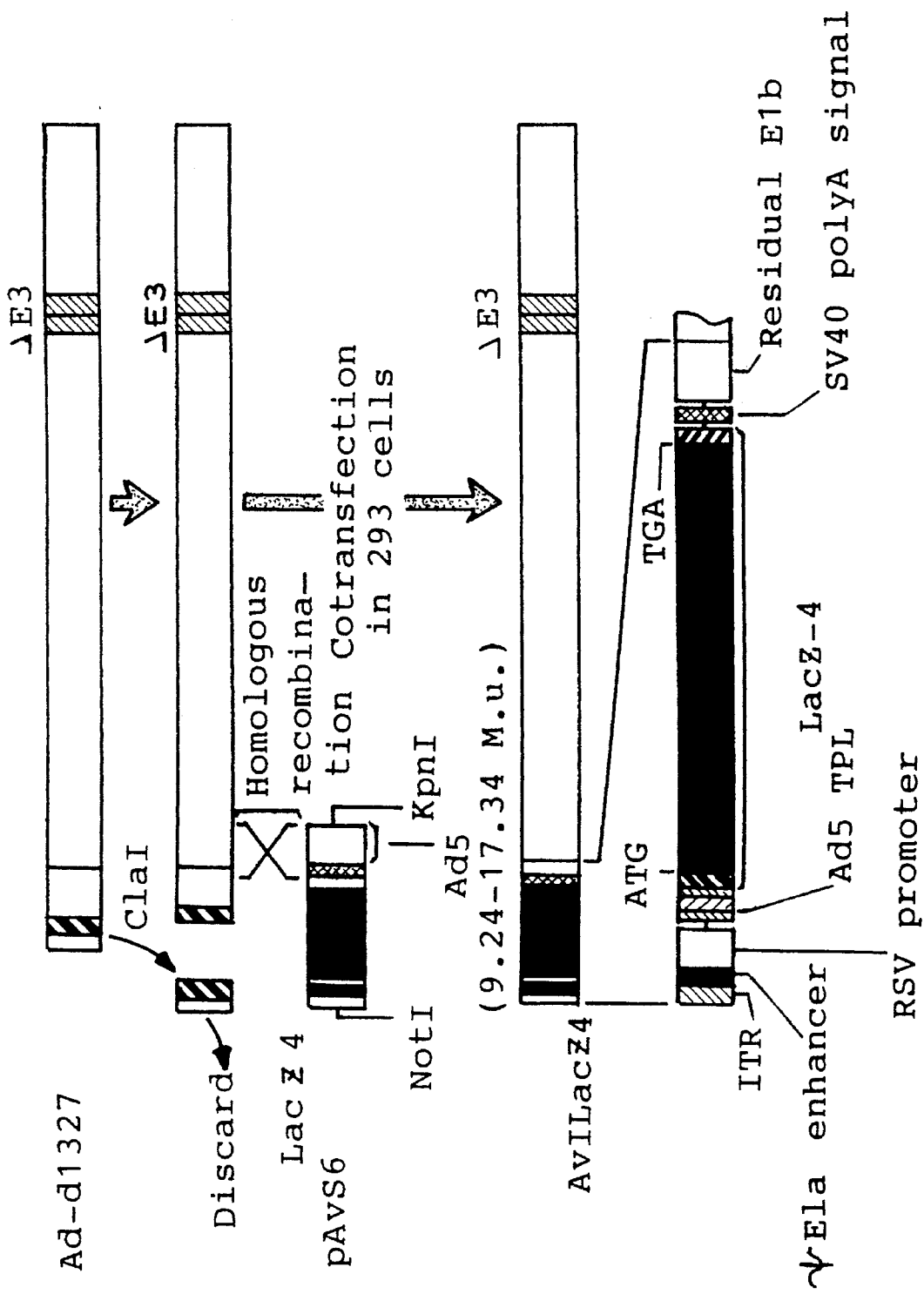
FIG. 6 is a schematic of the construction of Av1LacZ4.

Five micrograms of linearized plasmid DNA (pAvS6n-LacZ) and 2.5 µg of the large ClaI fragment of Ad-dl327 then were mixed and co-transfected into a dish of 293 cells by the calcium phosphate precipitation method. After 16 hours, the cells were overlaid with a 1:1 mixture of 2% Sea Plaque agar and 2× medium and incubated in a humidified, 37° C., 5% $CO_2$/air environment until plaques appeared (approximately one to two weeks). Plaques were selected and intracellular vector was released into the medium by three cycles of freezing and thawing. The lysate was cleared of cellular debris by centrifugation. The plaque (in 300 µl) was used for a first round of infection of 293 cells, vector release, and clarification as follows:

One 35 mm dish of 293 cell was infected with 100 µl of plaque lysate plus 400 µl of IMEM-2 (IMEM plus 2% FBS, 2 mM glutamine (Bio Whittaker 046764)) plus 1.5 ml of IMEM-10 (Improved minimal essential medium (Eagle's) with 2× glutamine plus 10% vol./vol. fetal bovine serum plus 2 mM supplemental glutamine (Bio Whittaker 08063A) and incubated at 37° C. for approximately three days until the cytopathic effect, a rounded appearance and "grapelike" clusters, was observed. Cells and supernatant were collected and designated as CVL-A. Av1LacZ4 vector (a schematic of the construction of which is shown in FIG. 6) was released by three cycles of freezing and thawing of the CVL-A. Then, a 60 mm dish of 293 cells was infected with 0.5 ml of the CVL-A plus 3 ml of IMEM-10 and incubated for approximately three days as above. Cells and supernatant from this infection then were processed by three freeze/thaw cycles in the same manner. Av1LacZ4 also is described in Yei, et al., Human Gene Therapy, Vol. 5, pgs. 731–744 (1994); Trapnell, Advanced Drug Delivery Reviews, Vol. 12, pgs. 185–199 (1993), and Smith, et al., Nature Genetics, Vol. 5, pgs. 397–402 (December 1993), which are incorporated herein by reference.

The resultant viral stocks were titered by plaque assay on 293 cells using a standard protocol involving a 1.5 hour adsorption period in DMEM/2% FBS, followed by washout and agar overlay of the cell monolayer. (Graham, et al., Virology, Vol. 52, pgs. 456–467 (1973)). The absence of wild-type virus was checked by polymerase chain reaction assays of these stocks using primers amplifying a 337 bp fragment of the E1 gene. All stocks were negative for wild-type adenovirus using this assay.

Adenoviral vector morphology and integrity were evaluated by high-resolution scanning electron microscopy. Briefly, bovine aortic smooth muscle cells were plated on silicon chips (Ted Pella, Inc., Redding, Calif.) for scanning electron microscopic evaluation of recombinant viral morphology and binding, and incubated for variable time periods to allow attachment. The chips then were exposed to medium containing virus at a concentration of $10^9$ iu/ml for periods ranging from 1 to 45 minutes, and subsequently were washed with PBS and fixed for 18 hours with 1% glutaraldehyde in sodium cacodylate at pH 7.4. After fixation, specimens were washed with distilled water and stained with 1% $OsO_4$ in distilled water for 30 minutes before a final wash, dehydration, and critical point drying. Specimens then were coated with a 1 nm continuous film in a Denton DV-602 sputter system (Morristown, N.J.). Specimens were staged in the lens of a Topcon DS-130 Schottky field emission scanning electron microscope operated at 25 kV. For transmission electron microscopy, the purified high titer stock of Av1LacZ4 was thawed, diluted 1:50 in ultrapure $H_2O$, spread onto grids, and negatively stained with 1% methylamine tungstate. Preparations then were evaluated using a Hitachi HU-12A electron microscope at 75 kV.

B. Aortic Smooth Muscle Cell Culture

Bovine aortic smooth muscle cells (BASMC) were obtained by outgrowth from medial explants of thoracic aortae of cows within 4 hours of slaughter. (March, Circulation Research, Vol. 72, pgs. 413–423 (1993)) and cultured in DMEM contianing 10% FBS, 2 mM glutamine, 100 ug/ml penicillin, 100 µg/ml streptomycin (DMEM-10) in a humidified, 5% $CO_2$ atmosphere at 37° C. Media were changed every 2 to 3 days. Cultures were passaged immediately prior to full confluence by brief exposure to HBSS containing trypsin (0.5 mg/ml) and EDTA (0.5 mM). All experiments were performed using cells of passage 7 or less. Cells were counted and assessed for trypan blue exclusion with a hemocytometer at each passage, routinely showing greater than 95% of the population to exclude trypan blue. BASMC were plated at a density of 25,000 cells/cm$^2$ and exhibited morphologic characteristics typical of vascular smooth muscle cells. Specifically, this included a pattern of multilayered growth, and a typical pattern of immunoperoxidase staining by a monoclonal antibody reactive with muscle α-actin (HHF-35) which does not react with endothelial cells (Tsukada, et al., *Am. J. Pathol.,* Vol. 127, pgs. 51–60 (1987)).

A protocol similar to the above was followed for the culturing of porcine aortic smooth muscle cells.

C. Transduction of Smooth Muscle Cells

Bovine aortic smooth muscle cells were plated in 6-well plates (surface area 9.8 cm$^2$), and allowed to attach at least overnight. The cells were plated at a density of 25,000 cells/cm$^2$.

Baseline conditions for transduction involved cell exposure to vector stock at a concentration of 2×10$^7$ pfu/ml for periods of time up to 120 minutes in 1 ml/well DMEM containing 2% FBS (DMEM-2), followed by two washes and replacement with DMEM-10. The transductions with Av1LacZ4 in the presence of 15 g % poloxamer 407 (BASF, Parsippany, N.J.) were carried out in media prepared by mixing the vector pre-diluted in DMEM-2, with stocks prepared by dissolving the poloxamer 407 at concentrations of 20 to 30 g % at 4° C. with intermittent agitation to avoid gel formation. (Johnston, et al., *J. Parenter. Sci. Technol.,* Vol. 39, pgs. 83–89 (1985)). The final concentration of poloxamer 407, after mixing the poloxamer 407 with the vector stocks, is 15 g %.

After transduction, the cells were washed twice with PBS, incubated for 48 hours, stained, and evaluated for transduction efficiency. The cells were fixed in 2.5% paraformaldehyde/0.5% glutaraldehyde in phosphate-buffered saline (PBS) for 5 minutes at 4° C. Subsequent staining was carried out overnight using X-Gal (5 mM potassium ferrocyanide, 5 mM ferricyanide, 2 mM magnesium chloride, and 1 mg/ml X-gal in PBS) at pH 7.4, 37° C., for 12 hours. (Dannenberg, et al., *Methods for Studying Mononuclear Phagocytes;* Adams, et al., eds. Academic Press, Inc., New York, 1981). The cells then were exposed to 1 μg/ml 4', 6-diamino-2-phenylindole (DAPI) in PBS for 5 minutes to stain all nuclei for fluorescent microscopic counting, and then stored under PBS/1 mM NaN$_3$. Total cell counts were determined by counting of all nuclei as a sum of those visualized by fluorescent excitation at 420 nM and those visualized by blue staining with clear nuclear predominance visualized under bright-field illumination (Fluovert, Leitz, Cambridge, England). These latter were interpreted as representing β-galactosidase gene transduction events, and the percentage of nuclear-positive blue cells was determined for each of 15 to 30 fields of 100× or 400× magnification, as appropriate. In cases of relatively low transduction rates, entire wells were scored for β-galactosidase positive cells. The results are shown in FIG. 7.

Figure 7:
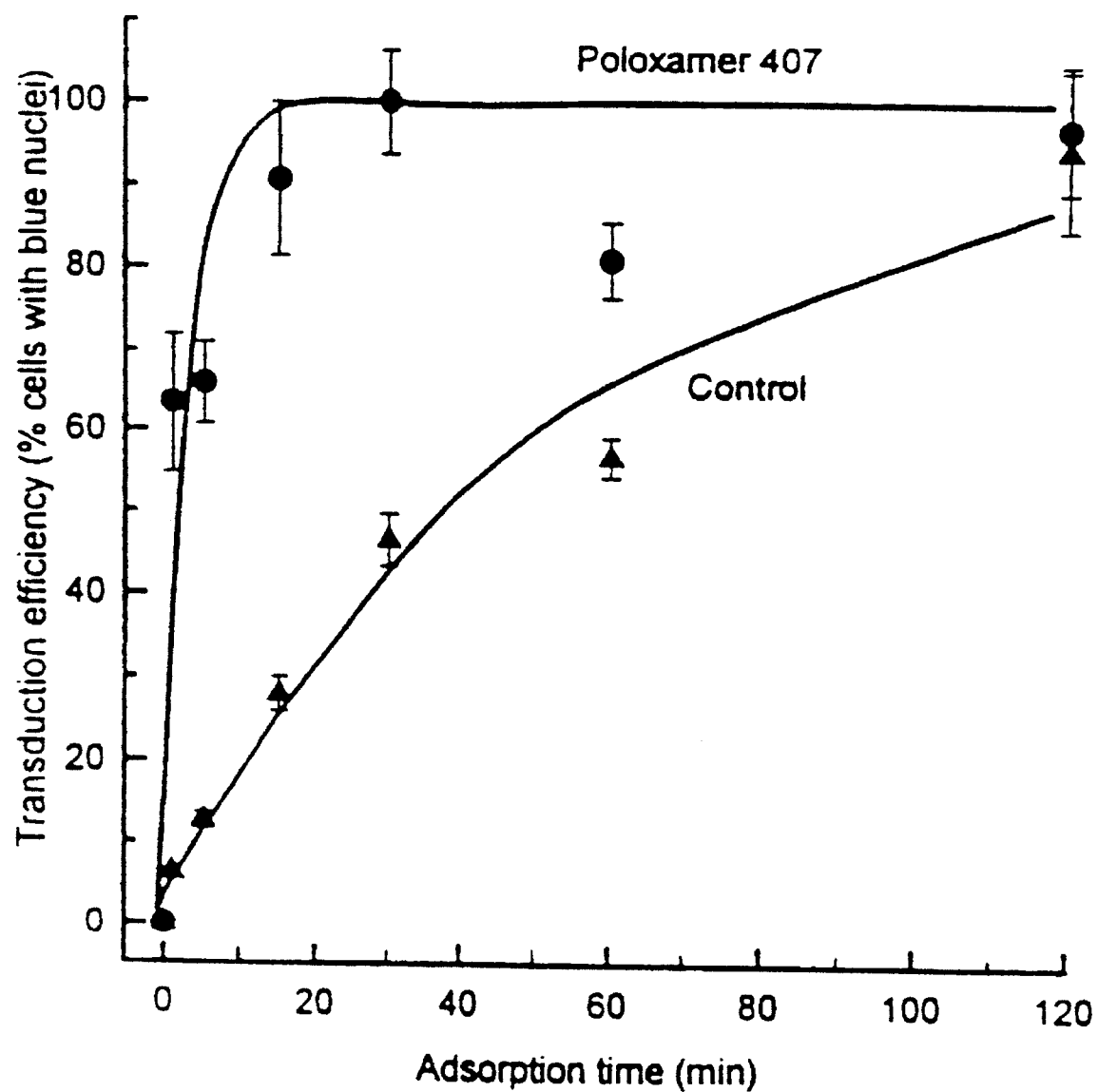
FIG. 7 is a graph of adsorption time versus transduction efficiency for bovine aortic smooth muscle cells transduced with Av1LacZ4 in the presence or absence of Poloxamer 407.

As shown in FIG. 7, the initial observed transduction rate, and consequently the transduction efficiency at any given time, was enhanced by a factor of from 10 to about 30 when the vectors were transduced into the cells in the presence of Poloxamer 407.

Example 2

Adsorption of Av1LacZ4, at concentrations up to 1.5×10$^9$ iu/m into porcine aortic smooth muscle cells (cultured and concentrated for adsorption as hereinabove described in Example 1 with respect to bovine aortic smooth muscle cells) were carried out in the presence or absence of 15% Poloxamer 407, in a constant volume of 1 ml at a density of 25,000 cells/cm$^2$. The adsorptions were carried out for 5 minutes. After the adsorptions, the cells were washed twice with PBS, incubated for 48 hours, stained, and evaluated for transduction efficiency as hereinabove described in Example 1. The results are shown in FIG. 8.

Figure 8:
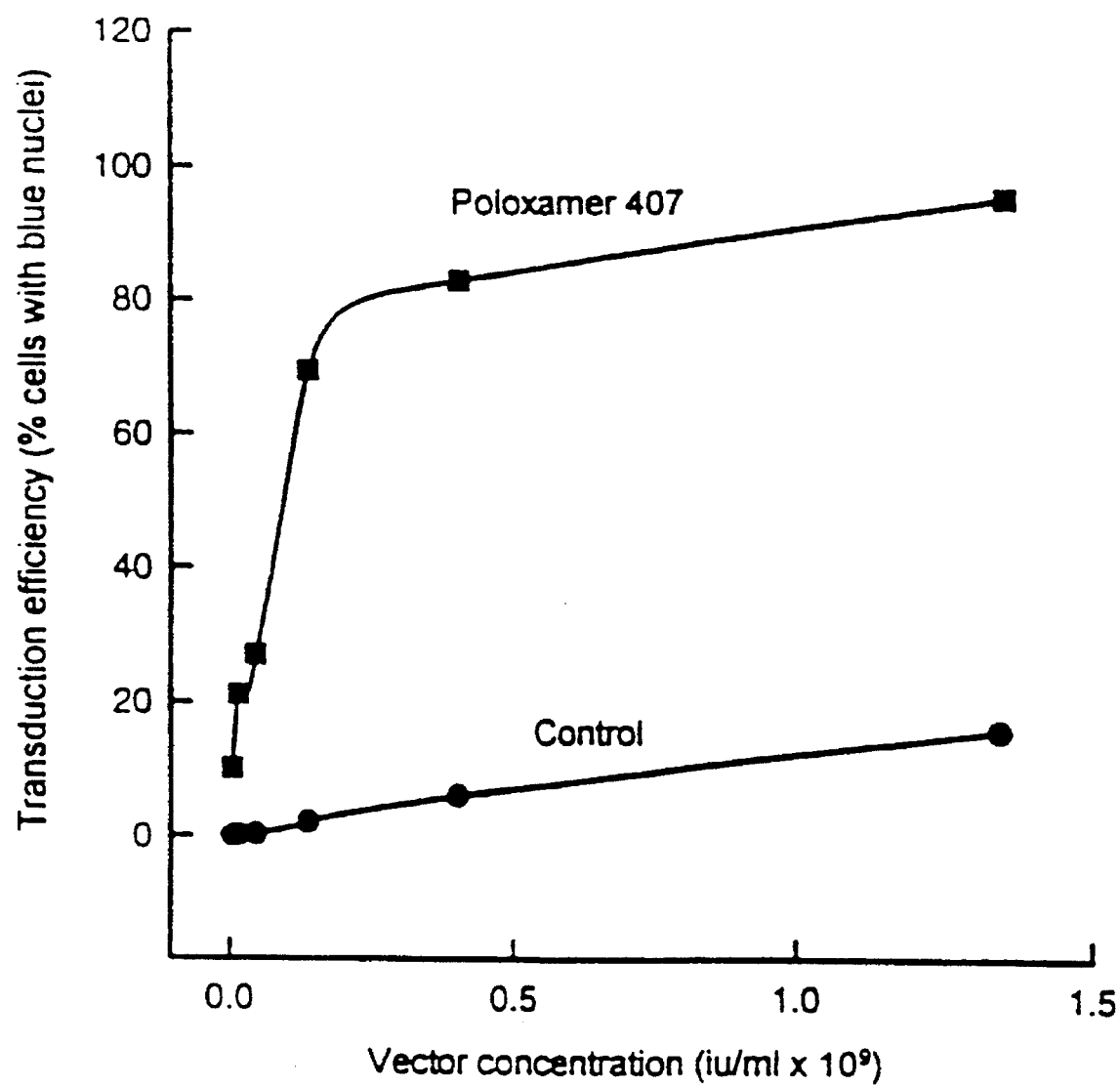
FIG. 8 is a graph of vector concentration versus transduction efficiency for porcine aortic smooth muscle cells transduced with Av1LacZ4 in the presence or absence of Poloxamer 407.

As shown in FIG. 8, greater transduction efficiency was achieved at all vector concentrations when the cells were transduced in the presence of Poloxamer 407, as compared with transduction in the absence of Poloxamer 407.

Example 3

Adsorptions of Av1LacZ4, at a concentration of 1.36×10$^6$ pfu/ml into bovine aortic smooth muscle cells were carried out in the presence or absence of Poloxamer 407, for 2 hours in a constant volume of 1 ml of medium (as hereinabove described in Example 1) at a cell density of 25,000 cells/cm$^2$. Following adsorption, the vector suspension was removed, the cells were washed gently from 1 to 5 times with PBS, and incubated for 48 hours prior to the staining for the presence of nuclear-targeted β-galactosidase as described in Example 1. The transduction efficiencies are plotted as a function of the number of washes in FIG. 9.

Figure 9:
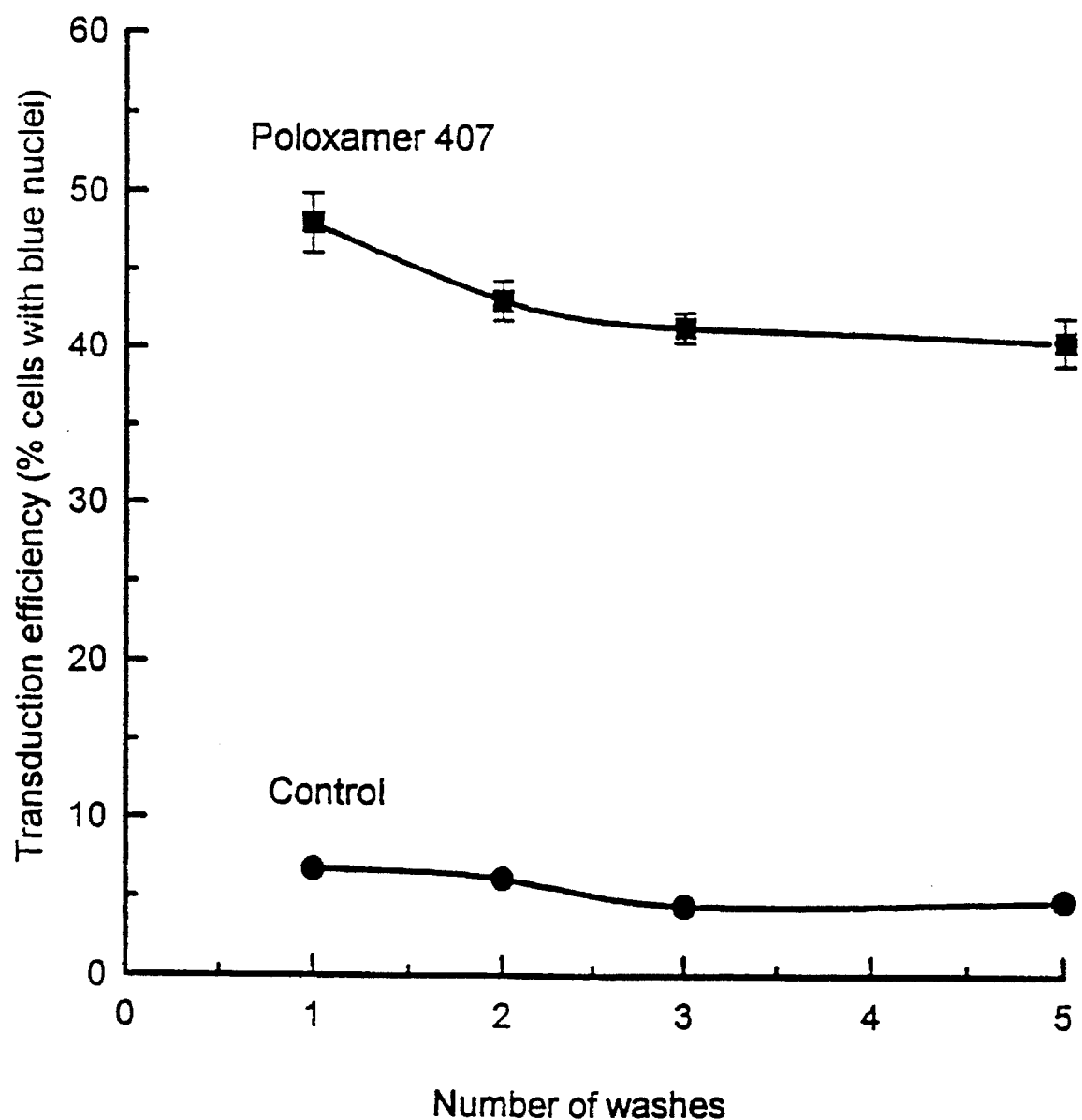
FIG. 9 is a graph of the number of washes versus transduction efficiency for bovine aortic smooth muscle cells transduced with Av1LacZ4 in the presence or absence of Poloxamer 407.

As shown in FIG. 9, greater transduction efficiency was achieved in the presence of Poloxamer 407 for each number of washes, as compared with transduction in the absence of Poloxamer 407.

The disclosure of all patents, publications (including published patent applications), and database entries referenced in this specification are specifically incorporated herein by reference in their entirety to the same extent as if each such individual patent, publication, and database entry were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. In a process for transfecting a cell with a viral particle, the improvement comprising:

contacting said cell with a composition comprising said viral particle and a non-ionic polyol, said non-ionic polyol being a polyoxyalkylene block copolymer wherein the alkylene moieties of the polyoxyalkylene groups each have from 2 to 5 carbon atoms, whereby said cell is transfected with said viral particle.

2. The process of claim 1 wherein said polyol is a polyoxypropylene-polyoxyethylene block copolymer.

3. The process of claim 1 wherein said polyol is present in an amount of from about 1 wt % to about 20 wt %.

4. The process of claim 3 wherein said polyol is present in an amount of about 15 wt %.

5. The process of claim 1 wherein said viral particle is an adenoviral vector particle.

6. The process of claim 1 wherein said viral particle is a retroviral vector particle.

7. The process of claim 1 wherein said polyol is present in an amount of from about 30 wt. % to about 40 wt. %.

8. The process of claim 1 wherein said cells are vascular cells.

9. A composition comprising a viral particle and a non-ionic polyol, said non-ionic polyol being a polyoxyalkylene block copolymer wherein the alkylene moieties of the polyoxyalkylene groups each have from 2 to 5 carbon atoms, and said viral particle being capable of transfecting a cell.

10. The composition of claim 2 wherein said polyol is a polyoxypropylene-polyoxyethylene block copolymer.

11. The composition of claim 9 wherein said polyol is present in an amount of from about 1 wt % to about 20 wt %.

12. The composition of claim 11 wherein said polyol is present in an amount of about 15 wt %.

13. The composition of claim 9 wherein said viral vector is an adenoviral vector particle.

14. The composition of claim 9 wherein said viral particle is a retroviral vector particle.

15. The composition of claim 9 wherein said polyol is present in an amount of from about 30 wt. % to about 40 wt. %.

* * * * *